United States Patent [19]

Wilkins et al.

[11] Patent Number: 4,713,240

[45] Date of Patent: Dec. 15, 1987

[54] VACCINES BASED ON INSOLUBLE SUPPORTS

[75] Inventors: Tracy D. Wilkins, Blacksburg; David M. Lyerly, Radford, both of Va.

[73] Assignee: Research Corporation, New York, N.Y.

[21] Appl. No.: 719,775

[22] Filed: Apr. 4, 1985

[51] Int. Cl.[4] ............................................. A61K 39/08
[52] U.S. Cl. ..................................... 424/92; 424/88; 424/89; 424/78; 424/81; 424/93; 514/2; 435/243; 435/253; 435/256; 435/258; 435/177; 435/178; 435/180
[58] Field of Search ....................... 424/88, 89, 92, 78, 424/81, 93; 514/2; 435/177, 178, 180, 179, 243, 181, 235, 253, 256, 258, 822, 911, 947, 948, 842; 436/540–531

[56] References Cited

U.S. PATENT DOCUMENTS

| 4,182,695 | 1/1980 | Horn et al. | 424/85 |
|---|---|---|---|
| 4,225,581 | 9/1980 | Kreuker et al. | 424/89 |
| 4,289,688 | 9/1981 | Hotta et al. | 260/112 R |
| 4,493,825 | 1/1985 | Platt et al. | 424/89 |
| 4,496,689 | 1/1985 | Metra | 260/112 R |
| 4,504,582 | 3/1985 | Swann | 424/78 |
| 4,606,918 | 8/1986 | Allison et al. | 424/88 |
| 4,609,546 | 9/1986 | Hiratani | 424/85 |

FOREIGN PATENT DOCUMENTS

| 0880427 | 11/1981 | U.S.S.R. | 424/78 |
|---|---|---|---|
| 1007676 | 3/1983 | U.S.S.R. | 424/88 |

OTHER PUBLICATIONS

Okita et al., CA, vol. 102, 1985, #2196221.
Chem. Abst., vol. 72, 1970, #63566w, Avrameus et al., "Method of Fixing Active Peptides on a Carrier".

Primary Examiner—John Kight
Assistant Examiner—Garnette D. Draper
Attorney, Agent, or Firm—Scully, Scott, Murphy & Presser

[57] ABSTRACT

The present invention relates to vaccine compositions which comprise at least one antigen chemically linked to a water-insoluble support combined with a pharmaceutically acceptable carrier. It also relates to a method of stimulating an organism's immune system by administration of these vaccine compositions.

10 Claims, 1 Drawing Figure

Dilution of mouse serum used in enzyme immunoassay

VACCINES BASED ON INSOLUBLE SUPPORTS

FIELD OF THE INVENTION

The present invention relates to vaccines and a method for their preparation. More particularly, it relates to vaccine preparations based on insoluble supports.

BACKGROUND OF THE INVENTION

Since the late 1700's, when Edward Jenner observed that individuals that had been inoculated with cowpox exhibited subsequent immunity to a smallpox challenge, it has been known to confer resistance to disease by vaccination. The basic principle behind the practice of immunization is that the body's own immune system is stimulated to produce a humoral or cellular response against a specific disease-causing organism by exposing the system to an antigen of the causative agent without actually bringing on the full symptoms of the disease. With the humoral and/or cellular response thus elicited, the treated individual is then protected against a future exposure to the virulent pathogen.

Although the principle is a relatively simple one, the difficulties associated with the development of a vaccine which is both safe and effective are many. First, it must be ensured that the stimulatory antigen is no longer capable of causing the disease with which it is associated, or at most only causes subclinical symptoms. Some commonly employed methods of achieving this include: using killed or inactivated organisms (U.S. Pat. Nos. 3,975,517; 4,152,414), inactivating the specific toxin which causes symptoms (U.S. Pat. Nos. 4,029,765; 4,007,265), or in some manner reducing or eliminating the virulence of the living organism to be used in the vaccine (U.S. Pat. Nos. 3,944,469; 4,110,433). Each of these methods presents certain difficulties in that the procedure required may be costly and time consuming; the inactivation may also adversely affect the antigenicity of the toxin, or the avirulent organism may revert back to its virulent state once in the body. Another problem involved with vaccine preparation is providing an amount of antigen sufficient, or for a long enough period of exposure, to elicit the desired immune response. This can be difficult when using certain types of very expensive antigens, which are not only costly to produce in large amounts, but are also rapidly eliminated from the body when provided as a vaccine in the traditional manner. In order to augment the immunogenicity of certain types of antigen, they are often combined with adjuvants which will enhance antibody production (U.S. Pat. No. 4,152,423; 4,001,395; 4,094,971). These substances may not only be difficult and time-consuming to prepare, but also may act as irritants when injected, causing vaccination to be quite painful.

There has now been discovered a method of preparing vaccines which can solve one or both of the above problems. Observations made in connection with the present invention show that linking an antigen to an insoluble support or carrier can serve to increase the power of the antigen to induce antibody formation while at the same time prolonging the lifetime of the antigen in the body. This means that the amount of antigen required is lessened and reduces the need for repeated exposures. It has also been unexpectedly discovered that certain toxins may be used safely in this form without prior inactivation, thereby eliminating the need for chemical treatment which may also severely compromise the toxin's antigenicity.

BRIEF DESCRIPTION OF THE INVENTION

The present invention relates to a vaccine composition which comprises an immunogenic-effective amount of an antigen chemically linked to a water-insoluble support, in combination with a pharmaceutically acceptable carrier. It also teaches a method of stimulating an organism's immune system by administering to the organism an immunogenic-effective amount of an antigen chemically linked to a water-insoluble support.

It further relates to a process for the preparation of a vaccine composition which comprises chemically coupling an immunogenic-effective amount of an antigen to an insoluble support.

The present invention additionally provides an improvement in the method of making monoclonal antibodies by providing to the host organism to be used for the production of lymphocytes an antigen which is chemically linked to an insoluble support. It also relates to the monoclonal antibody produced by this process.

Figure 1:
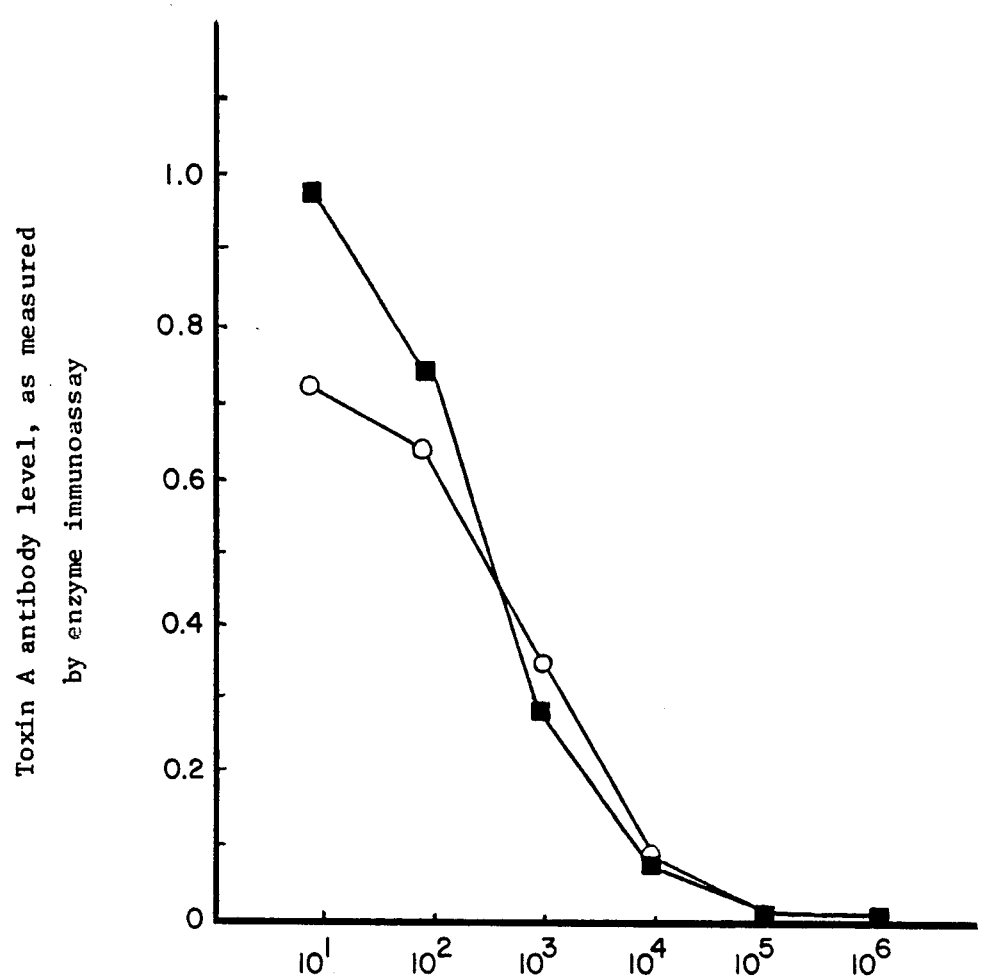
FIG. 1 shows antibody response of mice to two types of vaccines; Vaccine 1 is toxin A-Affigel 10 vaccine; Vaccine 2 is toxoid-A in adjuvant.

Group 1 mice ( ◯ ) were injected with a toxin A-bead vaccine (approximately 15 ug of active toxin A coupled to Affi Gel 10). Group 2 mice ( ■ ) were injected with a toxoid A-adjuvant vaccine (approximately 100 ug of inactivated toxin A in adjuvant). Both groups of mice received the same number of injections intraperitoneally over the same length of time. Each data point represents an average reading obtained from the sera of three different mice.

DETAILED DESCRIPTION OF THE INVENTION

The vaccine compositions of the present invention provide an efficient and safe means for highly effective stimulation of the body's immune response. The chemical linkage of the antigen of choice to the solid support allows the antigen to remain in the body for a longer period of time without clearance, thus giving a more prolonged exposure to the antigen, which in turn results in a more effective development of immunity.

In the present invention, the antigen of choice is chemically bound to a support which is insoluble or difficulty soluble in the body, i.e., water insoluble. The material used for the support may be any of the commonly known polymers, such as agarose, polyacrylamide, PVA, EVA, ethyl celluose acetate, microcrystalline cellulose, water insoluble polymers or copolymers of acrylic or methacrylic acid esters, and the like. It is of course preferred that the polymers used be in the form of small particles or beads to allow for more efficient distribution in the body from the point of administration and to minimize irritation upon injection. However, the main consideration in choosing the form to be used is that it is easily injectable. Particularly useful in the present invention are agarose beads, and specifically Affi-gel ® beads (Bio-Rad Laboratories, Richmond, Calif.). It is also obviously necessary that the polymer be pharmaceutically acceptable to the body. The antigen of choice may be either covalently bonded or chemically cross-linked with the polymer chosen. The term covalent bonding, as used in the present specification and claims, is understood to mean the direct chemical linking of the antigen with an insoluble carrier by covalent bonds. The term cross-linking is defined as the formation of intermolecular cross-linkages between the antigen and the carrier by use of a bi- or multifunctional reagent. Among the commonly used cross-linking agents are glutaraldehyde, isocyanate derivatives, bis-diazobenzidine, N,N'-ethylene bismaleimide, and N,N'-polymethylene bisiodoacetamide. The methods of covalent bonding are any of those well known in the art, and such procedures are also disclosed in any of the following U.S. Pat. Nos.: 3,555,143; 3,652,761; 3,645,852; 3,830,699, 3,788,948; 3,775,253; 3,654,090. The methods of cross-linking are also readily available to the skilled chemist (e.g. Chibata, I. *Immobilized Enzymes* Halstead Press, 1978). Of course, the preferred method to be used for binding the antigen varies depending on the nature of the antigen (i.e., glycoprotein, lipopolysaccharide, etc.) It is well within the skill of the experienced worker to determine which method is most suitable for use with the particular antigen and polymers of interest.

The term antigen as used in the present specification and claims is defined as any substance which an exposed organism is capable of recognizing and to which it can immunologically respond. As used in the present specification and claims, an immunogenic-effective amount of antigen is defined as that amount which will stimulate the body's B and T cells to initiate an immune response. This includes antigens of bacteria, viruses, fungi and protozoans. It also includes plant antigens, such as various types of grass or weed pollen, which are responsible for causing allergic reactions. Of course, there are a wide variety of different types of antigens; the most potent, for example, are proteins, glycoproteins and complex polysaccharides. Less immunogenic substances frequently found in the infective organisms include phospholipids, glycolipids, smaller, less complex carbohydrates and nucleic acids. As used herein antigen and immunogen are interchangeable. Excellent results are of course obtainable with the more potent immunogens; however, the attachment of the lesser immunogens to insoluble supports can serve to increase their immunogenicity. Similarly, it is also possible to attach non-antigenic portions of antigens to inert carriers to render them antigenic.

The method in which the antigens must be handled prior to binding to the inert support wall vary; certain types of antigens such as enzymatic bacterial toxins of the type found in, for example, *Clostridium perfringens* should be inactivated prior to immobilization on the support, since their activity will continue even after being bound. However, it has been unexpected discovered that it is possible to lower the level of tissue-damaging activity of certain non-enzymatic toxins to a level at which they are safe for internal administration, by binding them covalently to an insoluble carrier. This therefore provides a particularly simple method of vaccine preparation for organisms such as *Clostridium difficile* which have the appropriate type of toxin. Thus an even greater advantage is obtained because there is, in this case, no necessity for inactivation of the toxin, a process which frequently reduces the antigenicity of the toxin. The suitability of any type of toxin, or, in fact, any type of antigen, without inactivation may be readily and easily determined by binding the immunogen to beads, injecting it into an appropriate animal species and observing the result. The technique is described more specifically in Example 1. Other known microbial antigens, such as bacterial flagellar or pili antigens, which are not, on their own, disease-causing agents may also be readily combined with the insoluble supports without prior treatment.

In some cases, it may prove necessary to inactivate the antigen before administration. While inactivation of an antigen often results in a reduction of antigenicity, in the present invention, this problem is balanced by the increased antigenicity obtained by binding the antigen to a support. Inactivation may be done by a variety of methods well known in the art. Among the methods most frequently used are formaldehyde or formalin inactivation, exposure of whole cells to UV radiation, or heat treatment. The method of inactivation employed depends upon the type of antigen to be used. i.e., whether the immunogen is a portion of a whole cell, such as a toxin, or a whole cell or virus. As noted above, the present method is adaptable to a variety of antigens from different sources; among the types of antigens which can be usefully employed are bacterial toxins, capsular antigens, whole bacterial cells; whole virus particles or their antigenic protein components; protozoan toxins like "toxotoxin" from Toxoplasma, the antigenic glycoprotein coat of Leishmania or whole protozoan cells; or the antigens of the various infectious fungi such as yeasts. An additional application is the preparation of anti-allergy vaccines by the binding of one of the antigens associated with hay fever, for example, the pollens of ragweed or timothy grass, or one of their isolated antigens, such as antigen E. from Ambrosia, the dwarf ragweed. The methods of preparing and isolating the various microbial and plant antigens are well-documented in the scientific literature, and such techniques are readily available to the skilled artisan.

The compositions of the present invention also provide an improvement in the technology for the production of monoclonal antibodies. In the typical procedure for monoclonal antibody production a host organism is injected with antigen in order to stimulate the production of the desired antibody. This is followed by collection of lymphocytes from the organism's spleen, fusion of lymphocytes with an immortal cell line, and recovering a hybridoma. When the present composition is used as the antigen in the first step, much smaller amounts of pure antigen may be employed to achieve the same results as observed with more traditional techniques using unbound antigen. Also, because of the prolonged lifetime of the antigen in the body an increased number of antigen-specific B-lymphocyte blast cells in the spleen for use in fusion is observed.

This monoclonal technology can also be combined effectively with vaccine preparation. Specific monoclonal antibodies can be attached to an insoluble support, so that the combined antibody-support becomes a specific adsorbent for the antigen of choice. The desired antigen can then be readily purified from a complex mixture in a single simpler step. The resulting antibody-antigen-support complex can then be injected to elicit the appropriate antibody response in an animal, without the need for separation of the antigen from the antibody. In a case in which it is undesirable to have the antigen released in the body, such as in the case of toxins, the complex is covalently bonded to the support.

The methods for preparing the vaccine compositions are relatively simple. As noted above, the antigen or whole cells to be used may be isolated and/or inactivated, if necessary, by any of the methods known from the scientific literature. In many cases, it is not necessary to use a completely purified antigen. The antigen of choice is then simply combined with beads of the chosen support material and mixed for several hours, allowing binding to take place. Depending upon which specific type of support is being used, the support may require pre-treatment, or activation, in order to promote the binding to the support of the antigen. For example, treatment of agarose beads with cyanogen bromide as an activator is frequently employed to improve protein binding (P. Cuatrecasas et al., "Affinity Chromatography" in W. B. Jakob (Ed.), *Methods in Enzymology Vol.* XXII: 345–356, 1971). Some beaded supports, such as Affi-Gel or CNBr-activated Sepharose, come pretreated and require no additional activation. Similarly, if cross-linking is the method of binding to be employed, the cross-linking reagent employed will depend on the nature of the antigen and the type of support. It is within the skill of the experienced microbiologist to determine which of the available techniques will be most profitably employed for binding the antigen of choice. Following the period in which binding has occurred, the coupled antigen-bead complex is first washed with a substance, such as ethanolamine, which will block any remaining active sites on the support. The beads are then washed thoroughly with several volumes of an appropriate buffer in order to remove any unbound antigen. More than one antigen may be attached in this manner. The beads are then ready for use in a vaccine composition. It is possible, when binding is completed in a pharmaceutically acceptable medium, such as a phosphate buffered saline, to use the beads as is for injection into the subject. Alternatively, the beads may be combined with any of the commonly used excipients, as noted below.

The vaccine compositions of the present invention, because of their high level of antigenicity, do not have to be administered with any adjuvant. This of course obviates the problem of irritation which often accompanies the injection of a vaccine coupled of an adjuvant. The greater relative effectiveness of the present vaccines also means that the number of injections necessary can be reduced. A further advantage is found in that, because of the more effective immunogenicity observed, much smaller amounts of antigen can be employed. This becomes particularly important when the antigen is based on an expensive genetic recombinant microorganism, or a costly synthetic protein antigen. Because of their prolonged residence time in the body, the same desired result is obtained with relatively smaller amounts of the expensive antigen. It is also possible to combine several antigens as a single support to provide multiple vaccines as a single injection.

The compositions of the present invention are typically administered parenterally, e.g., subcutaneously intraperitoneally, intramuscularly, or intravenously. The antigen-support complex may be administered simply in combination with pharmaceutically acceptable carrier such as water, buffered saline, ethanol, polyol (for example, glycerol, propylene glycol, liquid polyethylene glycol and the like) suitable mixtures thereof, and vegetable oils. Where appropriate, the action of contaminating microorganisms can be prevented by various antibacterial and antifungal agents, such as parabens, chlorobutanol, phenol, sorbic acid, thimerosal, and the like. It will often be preferable to include isotonic agents, for example, glucose or sodium chloride.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the vertebrate subjects to be treated; each unit containing a predetermined quantity of active material calculated to produce the desired therapeutic effect in association with the required pharmaceutical carrier. The specification for the novel dosage unit forms of the invention are dictated by and directly dependent on the unique characteristics of the active material and the particular therapeutic effect to be achieved, and it is within the skill to the physician to determine the dose appropriate for the subject involved. Because of the excellent immunogenic effect observed with the present composition, and the high affinity of the beads for antigens, extremely small amounts of antigen may be coupled to do small volumes of beads for a single dose. As a typical example, 10 to 100 ul of of Affi-Gel ® beads combined with between 10 to 500 ug of *Clostridium difficile* toxin A represents an adequate single dose, depending of course on the size and type of organism being immunized. Dosage also varies depending on the antigen being used; the proper amount to be used, however, can readily be determined by standard immunological techniques.

The present vaccines are useful in treatment of human and non-human vertebrates. The possible range of applications will be readily apparent to one of ordinary skill in the art. These vaccines are particularly useful in the field of veterinary medicine where farm animals may be adversely affected by an excessive amount of handling. For example, over 90% of the farm animals in the United States are vaccinated against clostridial toxins each year. Certain very valuable animals such as minks are extremely sensitive to stress such as that which may be caused by multiple immunizations. Because of the unusual effectiveness of the present vaccines in eliciting an immune response the necessity for a large number of vaccinations will be reduced; therefore, the loss of livestock resulting from excessive handling and stress should be correspondingly reduced.

The nature of the present invention will be more readily understood with reference to the following non-limiting examples:

EXAMPLE 1

The following example illustrates the process of preparing a *Clostridium difficile* vaccine.

Affi-Gel 10 (Bio-Rad Laboratories location) beads were washed with deionized, distilled water, and then combined with homogeneous toxin A derived from *C. difficile* 10463, as described in Sullivan et al., *Infect. Immuno.* 35: 1032–1040, 1982. The bead suspension was then mixed for at least 1 hour, or overnight, to allow covalent bonding between antigen and beads. Subsequent to mixing, any remaining active sites on the beads are blocked by addition of a volume of ethanolamine for 1 hour. After the antigen was bound and the remaining sites blocked, the beads were washed with 5-10 bed volumes of phosphate buffered saline (at least 0.5M NaCl), to remove any unbound antigen from the beads. The beads at this stage are ready for administration in the saline solution, or may be combined with any other acceptable carrier.

EXAMPLE 2

This example demonstrates to the increase in antigenicity and decrease in toxicity observed in binding a Clostridium toxin to an insoluble support.

BALB/c mice were divided into two groups. Group 2 was injected intraperitoneally with 100 ug of toxoid A (i.e., toxin A of *Clostridium difficile* which has been inactivated with formalin); Group 1 was injected intraperitoneally with 15 μg of a toxin A Affin-Gel®10 vaccine as prepared in Example 1. Both groups received the same number of injections, once every week over a period of two months. Serum samples were taken from the mice and analyzed for antibodies against toxin A (See FIG. 1). Both groups showed similar levels of toxin A antibodies, although the amount of toxin A administered to Group 1 mice was 6 times higher than that adminstered to Group 2 mice, thus demonstrating the ability of the bead vaccine to elicit antibody response.

To test comparative toxicity, mice were again divided into two groups. Group 1 mice were injected with 100 ng of *Clostridium difficile* toxin A; all mice thus treated died within 24 hours. Group 2 mice were injected with 15 μg of toxin A bound to Affi-Gel®10 beads; this represents 150 times the normally lethal amount of toxin A. None of the mice treated in this manner died following treatment, thus showing a significant decrease in toxic activity of the toxin when bound to an insoluble support. Injection of 500 ug of toxin coupled to beads, 5000 times the lethal dose, does result in the death of the mice, however.

EXAMPLE 3

This example illustrates the process of preparing a monospecific antiserum using a bead vaccine.

A 1-year-old Alpine Nubian male goat was injected with toxoid A mixed 1:1 with incomplete Freund adjuvant, to prime the animal prior to administration of the support bound active toxin; the low level of antibody produced by this treatment serves to minimize any tissue damage caused by the active toxin. The goat received about 1 mg of toxoid A subcutaneously once each week for 4 weeks; it was then injected with active toxin A bound to Affi-Gel 10 (Bio-Rad Laboratories location). The goat received 1 ml of a 10% suspension of the toxin A-gel (ca. 0.1 mg of toxin A protein) once each week for 6 weeks. The antiserum was brought to 50% saturation with a solution of 100% saturated $(NH_4)_2SO_4$. The precipitated was collected, dissolved in PBS. The preparation was passed through a 0.45-um membrane and stored at 4° C.

Table 1 shows typical antibody responses observed using a number of different animals and toxins.

| Vaccine | animal | response |
|---|---|---|
| toxin A-Affi Gel 10 (390 μg/injection) | rabbit | monospecific antiserum against toxin A |
| toxin A-Affi Gel 10 (200 μg/injection) | goat | monospecific antiserum against toxin A |
| toxin A-Affi Gel 10 (15 μg/injection) | mouse | monospecific antiserum against toxin A; as good as mice vaccinated with 100 μg toxoid A-adjuvant |
| nontoxic antigens-Affi Gel 10 (9 mg/ml) | rabbit | immunoprecipitating antibody against nontoxigenic *C. difficile* |
| nontoxic antigens-Affi Gel 10 (9 mg/ml) | goat | immunoprecipitating antibody against nontoxigenic *C. difficile* |
| *C. spiroforme* antigen-Affi Gel 10 | rabbit | rabbit vaccinated 3 times over 2.5 months showed good levels of immunoprecipitating antibody |

What is claimed is:

1. A vaccine composition useful in initiating an immune response against an organism of the genus Clostridium which comprises an immunogenic-effective amount of at least one non-enzymatic toxin of said organism covalently bonded or cross-linked to a water-insoluble support, in combination with a pharmaceutically acceptable carrier.

2. The composition of claim 1 wherein the toxin is derived from *Clostridium difficile.*

3. The composition of claim 2 wherein the toxin is toxin A.

4. The composition of claim 1 wherein the insoluble support is agarose, polyacrylamide, PVA, EVA, ethyl cellulose, acetate, microcrystalline cellulose or a polymer or copolymer of acrylic or methacrylic acid esters.

5. The composition of claim 4 wherein the insoluble support is agarose.

6. The composition of claim 5 wherein the insoluble support is in bead form.

7. A method for stimulating an organism's immune response against Clostridium which comprises administering to said organism an immunogenic-effective amount of at least one non-enzymatic antigenic toxin of Clostridium covalently bonded or cross-linked to a water-insoluble support, in combination with a pharmaceutically acceptable carrier.

8. The method of claim 7 wherein administration is parenteral.

9. The method of claim 7 wherein administration is subcutaneous, intramuscular, intraperitoneal or intravenous.

10. The method of claim 9 wherein administration is subcutaneous.

* * * * *